United States Patent [19]

Heyl et al.

[11] Patent Number: 5,080,800
[45] Date of Patent: Jan. 14, 1992

[54] PROCESS FOR REMOVING COMPONENTS FROM SOLUTIONS

[75] Inventors: Barbara L. Heyl, Atlanta; Lynn C. Winterton, Roswell; Kai C. Su, Alpharetta; Jack C. White, Stone Mountain, all of Ga.

[73] Assignee: Ciba-Geigy Corporation, Ardsley, N.Y.

[21] Appl. No.: 671,967

[22] Filed: Mar. 18, 1991

Related U.S. Application Data

[62] Division of Ser. No. 461,988, Jan. 8, 1990.

[51] Int. Cl.$^5$ .............................................. B01D 15/00
[52] U.S. Cl. .................................. 210/679; 210/681; 210/683; 210/692; 210/903
[58] Field of Search ............... 210/660, 679, 681, 683, 210/691, 692, 902, 903, 908, 909

[56] References Cited

U.S. PATENT DOCUMENTS

| | | | |
|---|---|---|---|
| 2,061,958 | 11/1936 | Chapman | 215/37 |
| 2,160,602 | 5/1939 | Nagel | 65/45 |
| 2,761,833 | 9/1956 | Ward | 222/189 |
| 3,346,146 | 10/1967 | Thompson | 222/189 |
| 3,361,304 | 1/1968 | Thompson | 222/189 |
| 3,422,993 | 1/1969 | Boehm et al. | 222/190 |
| 3,622,049 | 11/1971 | Thompson | 222/190 |
| 3,760,987 | 9/1973 | Meterhoefer | 222/153 |
| 3,951,798 | 4/1976 | Haldopoulos | 210/452 |
| 3,977,560 | 8/1976 | Stumpf et al. | 222/189 |
| 3,985,271 | 10/1976 | Gardner | 222/190 |
| 4,002,168 | 1/1977 | Petterson | 128/233 |
| 4,013,410 | 3/1977 | Thomas et al. | 21/58 |
| 4,018,364 | 4/1977 | Wright | 222/190 |
| 4,115,272 | 9/1978 | Mukhamedyarov et al. | 210/266 |
| 4,131,544 | 12/1978 | Elahi | 210/40 |
| 4,184,615 | 1/1980 | Wright | 222/190 |
| 4,231,872 | 11/1980 | Keil | 210/93 |
| 4,250,141 | 2/1981 | Lehmann et al. | 422/44 |
| 4,259,184 | 3/1981 | D'Arnal | 210/85 |
| 4,276,160 | 6/1981 | Donnert et al. | 210/660 |
| 4,338,194 | 7/1982 | Tanny | 210/490 |
| 4,368,081 | 1/1983 | Hata et al. | 134/2 |
| 4,396,583 | 8/1983 | LeBoeuf | 422/301 |
| 4,463,880 | 8/1984 | Kramer et al. | 222/189 |
| 4,521,375 | 6/1985 | Houlsby | 422/29 |
| 4,529,511 | 7/1985 | Breeden et al. | 210/94 |
| 4,530,963 | 7/1985 | DeVoe et al. | 525/54.1 |
| 4,537,683 | 8/1985 | Isacoff et al. | 210/667 |
| 4,560,491 | 12/1985 | Sherman | 252/106 |
| 4,568,517 | 2/1986 | Kaspar et al. | 422/30 |
| 4,578,187 | 3/1986 | Alhäuser | 210/93 |
| 4,711,718 | 12/1987 | Nelson, Jr. | 210/282 |
| 4,714,550 | 12/1987 | Malson et al. | 210/244 |
| 4,721,624 | 1/1988 | Schumann | 426/286 |
| 4,747,954 | 5/1988 | Vaughn et al. | 210/670 |
| 4,756,833 | 7/1988 | Schlossel | 210/662 |
| 4,758,351 | 7/1988 | Kern | 210/688 |
| 4,789,475 | 12/1988 | Harte et al. | 210/502.1 |
| 4,792,403 | 12/1988 | Togo et al. | 210/692 |
| 5,013,459 | 5/1991 | Gettings et al. | 210/282 |

FOREIGN PATENT DOCUMENTS

| | | |
|---|---|---|
| 427392 | 4/1938 | Belgium . |
| 8622273 | 7/1989 | Fed. Rep. of Germany . |
| 1227667 | 8/1960 | France . |
| 8200128 | 1/1982 | PCT Int'l Appl. . |

*Primary Examiner*—Ivars Cintins
*Attorney, Agent, or Firm*—Wenderoth, Lind & Ponack

[57] ABSTRACT

A dispensing device having a container body defining a solution retaining chamber therein, the container having an outlet for dispensing the solution from the chamber and means for removing a component from the solution as the solution is dispensed from the chamber through the container outlet.

9 Claims, 3 Drawing Sheets

PROCESS FOR REMOVING COMPONENTS FROM SOLUTIONS

This application is a division of application Ser. No. 07/461,988 filed Jan. 8, 1990.

BACKGROUND OF THE INVENTION

The present invention relates to a solution dispenser, and more particularly to a dispenser in which preservatives and other components may be removed from the solution as a solution is dispensed.

Many solutions are available for making contact lenses more comfortable, safer, and easier to wear. For example, wetting solutions facilitate the wetting of a lens, soaking solutions serve as anti-microbial storage medium and prevent dehydration and distortion of the lens, and cleaning solutions remove accumulated eye secretions and other contaminants from lenses. A large number of other solutions are also used by contact lens patients. These ophthalmic solutions are typically marketed in squeezable plastic containers or aerosol cans having a nozzle through which the solution is dispensed.

Because these solutions come in contact either directly or indirectly with the eye, it is very important that they be free of microbial growth. To this end, it is common practice for preservatives to be provided in these solutions. Among the preservatives used in ophthalmic solutions are polymoxin B sulfate, quaternary ammonium compounds, chlorobutanol, organic mercurials, p-hydroxybenzoic acid esters, and certain phenyls and substituted alcohols.

A problem exists, however, in that the preservatives used in the ophthalmic solutions can cause eye irritation if used in high concentrations. For example, benzalkonium chloride (BAK) is used as a preservative in ophthalmic solutions and has broad anti-bacterial and anti-fungal activity when used with other components, such as disodium ethylene diaminetetraacetic acid (EDTA). However, it has been reported that repeated use of BAK can denature the corneal protein and cause irreversible eye damage. Also, in addition to chemical sensitivity, a number of contact lens wearers have allergic reactions to the preservatives used in ophthalmic solutions, even at relatively low concentrations.

The typical remedy for overcoming chemical sensitivity and allergic reactions to preservatives in ophthalmic solutions entails switching the patients to an unpreserved solution. However, unpreserved solutions present problems in marketing, as well as in home storage, in that once the container housing the solution is opened, the solution quickly becomes contaminated and unsuitable for further use. They also tend to be very expensive to produce.

Therefore, there exists a need for an apparatus which removes preservatives, as well as other components, from a solution as the solution is dispensed to a patient.

There exists a further need for such an apparatus which is easily manufactured and economical to use.

There exists a further need for an apparatus which may be attached to a standard solution container.

SUMMARY OF THE INVENTION

The present invention relates to a device for removing a component, including but not limited to preservatives, from ophthalmic and other solutions as the solution is dispensed from a container. The device preferably comprises a container having squeezable sidewalls defining a solution retaining chamber, but may also be an aerosol can or other container. The container also preferably includes a neck portion and a dispensing head having a container outlet on its end through which the solution is dispensed. Means for removing the component from the solution as the solution is dispensed from the chamber through the container outlet are also provided.

In a first embodiment, the means for removing a component from the solution comprise a scavenging material provided within the path of the solution as the solution is dispensed. In this embodiment, the device is a standard solution container housing a solution having the component to be removed, and the scavenging material is held within the dispensing head. The scavenging material may have a positive charge for scavenging negatively charged components or it may have a negative charge for scavenging positively charged components or it may be a material which selectively scavenges components by a size exclusion mechanism or it or may comprise any other means for removing a component from solution.

In an alternative embodiment, a fitment may be utilized having a fitment body which is releasably engagable with a standard solution container. The fitment includes passage means within its body for allowing passing of the solution from the container to a fitment outlet. In this embodiment, the means for removing a component may comprise a scavenging material provided within the fitment so as to be within the path of the solution as the solution is dispensed from the container outlet to the fitment outlet. The fitment has the advantage of being able to be adapted to standard solution containers.

Also, means for providing a control of the flow of solution out of the container may be provided. For example, a check valve may be provided within the final dispensing outlet to prevent backflow of solution into the container following use. Additionally, means for regulating the flow of air into the container, namely, a second check valve, may be placed within the neck portion of a squeezable container for allowing air to flow into a depressed container, thereby restoring the container to its original shape. This embodiment will minimize the incidence of microbial growth in the area of the dispensing head proximate the final dispensing outlet.

Therefore, it is an object of the present invention to provide an apparatus which removes preservatives, as well as other components, from a solution as the solution is dispensed to a patient.

It is also an object of the present invention to provide such an apparatus which is easily manufactured and economical to use.

It is also an object of the present invention to provide such an apparatus which may be adapted to a standard solution container. These and other objects and advantages will be more apparent from the following detailed description of the invention.

DETAILED DESCRIPTION OF THE INVENTION

Figure 5:
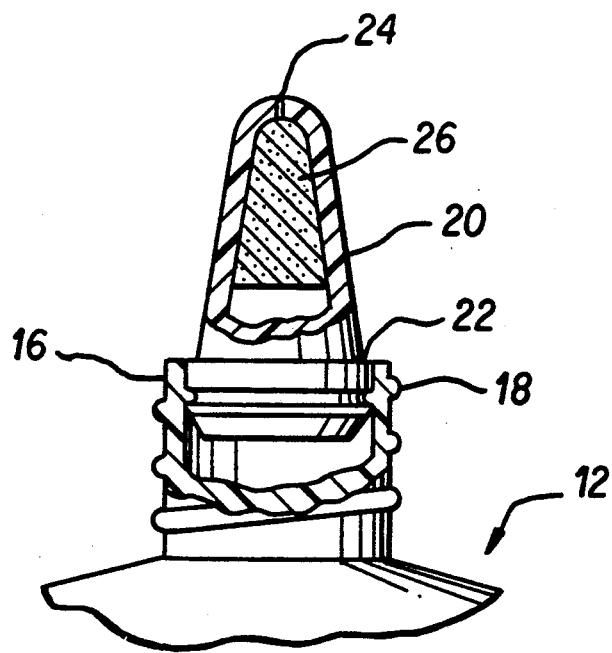
FIG. 5 is a partial cross-sectional view of an embodiment of the present invention in which the dispensing head is snap-fitted onto a container.
Figure 6:
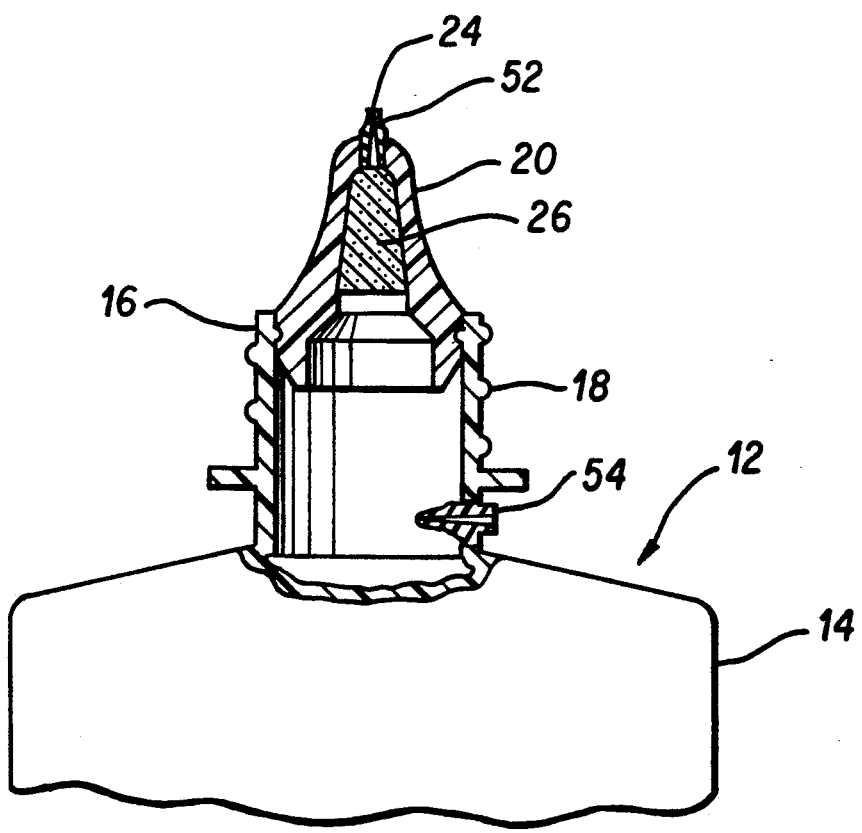
FIG. 6 is a partial cross-sectional view of an embodiment of the present invention having means for providing one-directional flow of solution out of a container.

Referring to the figures, a device 10 for removing components, such as preservatives, from solutions, such as an ophthalmic solution, is shown. The device 10 includes a container 12, preferably constructed of molded plastic, having resilient sidewalls 14 which define a solution retaining chamber and which preferably may be deformed by inward pressure to produce a pressure within the container 12 for using and dispensing its contents. The container 12 is provided with an upstanding neck portion 16 having external threads 18 thereabout. A dispensing head 20 is provided atop the neck portion 16, either integrally, as shown in FIGS. 1-4, by threading engagement, or by snap-fitting engagement as shown in FIGS. 5 and 6. A flange portion 22 is provided between the dispensing head 20 and the container neck 16. The dispensing head 20 has passage means, such as a duct or other passageway, through its length which in turn has a first end in communication with the chamber and a container outlet 24 at the other end.

Figure 1:
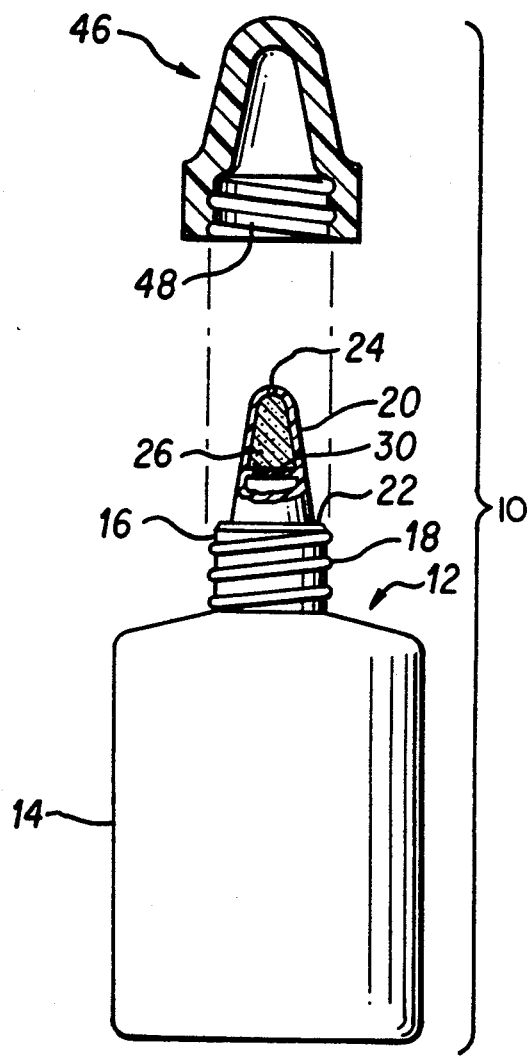
FIG. 1 is an exploded view of a first embodiment of the present invention in which scavenging material is provided within a container.
Figure 2:
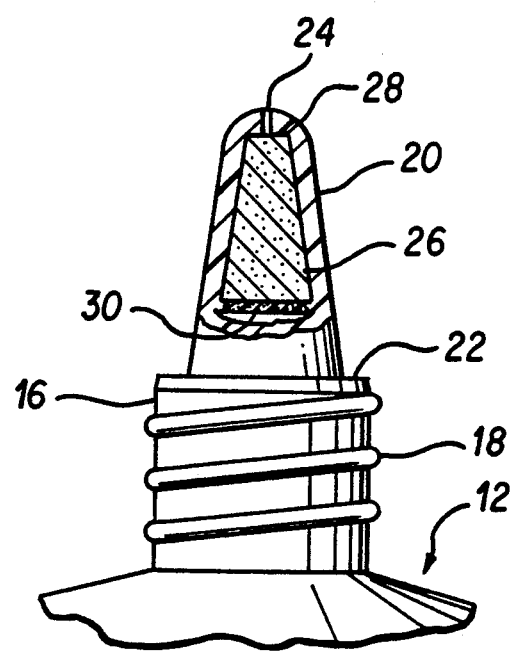
FIG. 2 is a partial cross-sectional view of a first embodiment of the present invention in which scavenging material is provided within a container.

In a first embodiment of the present invention, shown in FIGS. 1 and 2, means for removing preservatives or other components are placed directly within the dispenser head 20. In its preferred form, the preservative removing means comprise scavenging material 26 provided intermediate the chamber and the container outlet 24, so as to be within the path of the solution as the solution is dispensed from the container 12. The material 26 should be positioned as close as possible to the outlet 24 to minimize empty space in the upper portion of the dispensing head 20. The material 26 may be compressed into a porous mass which is preferably insert molded into the dispensing head 20. However, any other means of maintaining the material in the path of the solution may also be used. Alternatively, as shown in FIG. 2, the material 26 may be in the form of fine particles and held in place by porous supporting members 28 and 30. The members 28 and 30 may be made from porous plastic, such as porous polyethylene. In either case, it is important that the solution pass through the scavenging material 26 as it exits the container 12 so that the component is removed upon contact with the scavenging material 26.

Figure 3:
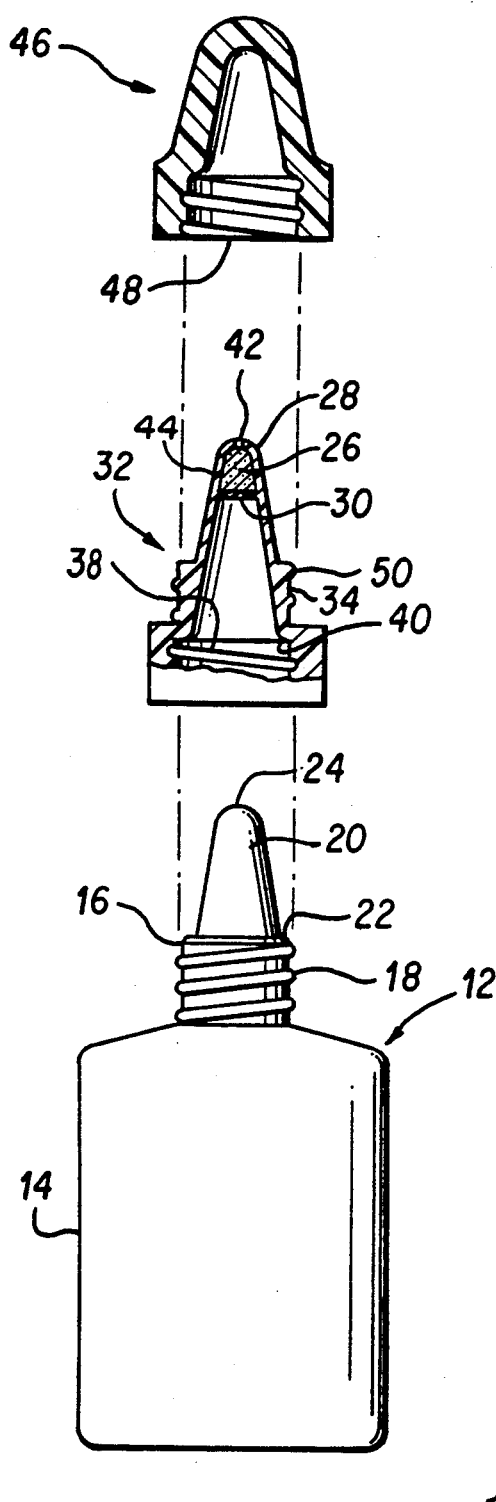
FIG. 3 is an exploded view of a second embodiment of the present invention in which scavenging material is provided within a fitment.
Figure 4:
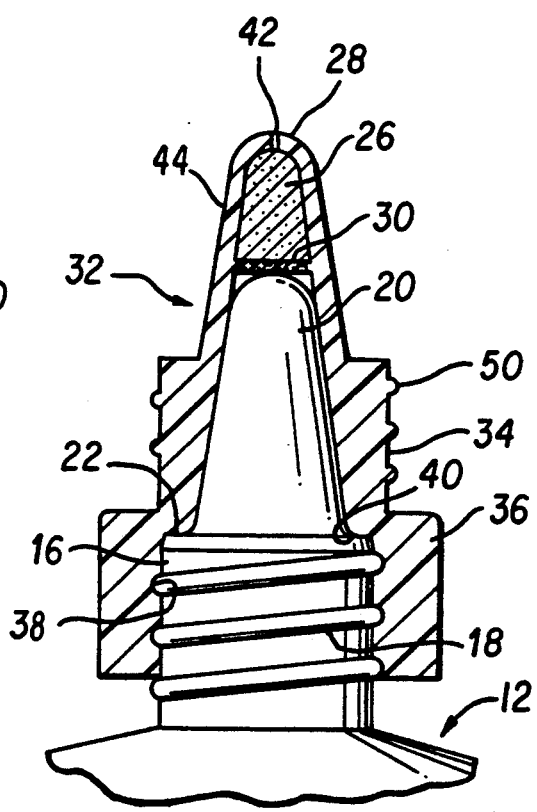
FIG. 4 is a partial cross-sectional view of a second embodiment of the present invention in which scavenging material is provided within a fitment.

A second embodiment of the invention, shown in FIGS. 3 and 4, includes a fitment 32 having a body 34 which is affixable to a standard-size container 12, such as described above but without the scavenging material 26 within its dispensing head 20. The lower portion 36 of the fitment 32 is provided with internal threads 38 which complimentarily mate with threads 18 on the outer surface of the neck portion 16 so that the fitment 32 may be releasably matable to the container 12. As seen in FIG. 4, when the fitment 32 is in threaded relationship with the container neck portion 16, an internal flange 40 of the fitment 32 rests atop the neck portion 16 to provide a seal between the fitment 32 and container 12. The fitment 32 has a fitment outlet 42 atop a tapered upper section 44, as well as a passage or duct through its length. The passage is preferably adjacent to and in flow registration with the container outlet 24 at one end and opens to the fitment outlet 42 at its other end. In this alternative embodiment, the scavenging material 26 is provided within the fitment 32, and removes the component, such as preservative, from the solution as the solution passes from the container outlet 24 to the fitment outlet 42. As in the first embodiment, the scavenger material 26 may be in solid mass or powder or other form.

FIG. 6 shows a device 10 of the present invention which includes means for providing one-directional flow of solution out of the container, such as a check valve 52. Preferably, the valve 52 is a deformable, polymeric valve that is positioned within the container outlet 24 so as to be in flow communication with the interior portion of the dispensing head 20 at one end and with the atmosphere at a second end. In its normal or closed position, the valve 52 does not allow air or solution to flow into or out of the container 12. However, as a result of the pressure exerted onto the container 12 during use, the valve 52 moves to an open position that allows the solution to pass through to the atmosphere. When the pressure on the container 12 is stopped, the valve 52 closes and any solution remaining atop the valve 52 cannot be pulled back inside the container 12, thereby minimizing the incidence of organisms reentering the container 12 after use.

Also, when a squeezable container 12 is used, means for drawing air into the container 12 may be provided for returning the container 12 to its original shape. Preferably, a second one way check valve 54 is provided within the neck portion 16 and below the scavenging material 26. Upon release of the container 12 by the user, air is drawn into the container 12 by the valve 54, thereby restoring the container 12 to its proper shape. Also, because the valve 54 is one-directional, solution from within the container 12 cannot leak out to the atmosphere through the valve 54. Furthermore, because the second valve 54 is below the scavenging material 26, any organism which should happen to be withdrawn into the container will be deposited into the preserved solution and killed.

Both the dispensing head 20 of the first embodiment and the fitment 32 of the second embodiment may include a closure cap 46. The closure cap 46 may have internal threads 48 capable of matingly engaging with either the threads 18 of the neck portion 16, as shown in FIG. 1, or the external threads 50 of the fitment 32, as shown in FIG. 3, and resting on flange 22.

Of course, containers other than squeezable plastic types may be utilized. The scavenging material may be placed within an aerosol type dispenser, a solid bottle, or some other container.

Virtually any type of scavenging material 26 for removing a preservative or other component from solution may be used. For example, removal of benzalkonium chloride or other quaternary ammonium compounds can be accomplished by an ionic exchange mechanism or chemical affinity, for example, using fumed silica. The scavenging material 26 would preferably be an inert material with a negative charge, and the positively charged quaternary ammonium compound would adhere to the material 26 as it flows through the fitment 32 or dispensing head 20, depending on the embodiment. Examples of products capable of removing positively charged preservatives such as BAK include AG-50X-8, AG-50X-16, BIO-BS-SM2, and BIO REX70, all available from BIO-RAD Laboratories, Richmond, California and Acropor 5A-6404 available from Gelman Sciences, Ann Arbor, Michigan. Similarly, negatively charged components, such as acids, may be removed by using positively charged scavenging material 26. Examples of such scavenging material includes AG-1, AG-2X8, and AG-10 Alumina from BIO-RAD Laboratories. For example, it has been found that scavenging material 26 comprising Chelex 100 from Bio Rad will remove Thimerosal from solution. Alternatively, the scavenging material may be porous plastic, such as porous polyethylene, imbedded with a cross-linked styrene divinyl benzene which is sulfonated to produce either a positively charged hydrogen form or a negatively charged sodium form. Other scavenging materials useful in the present invention are those relating to chemical affinity techniques, such as immunoassay, active site binding and affinity chromatography.

As one particular example, it has been found that a scavenging material comprised of a mixture of "Bio Rex 5" and "AG-4", both Bio Rad products, in a 75 to 25 ratio will almost completely remove 0.1% sorbic acid from a solution and raise the pH of the solution from 4.0 to 7.0. This is important since sorbic acid is a commonly used preservative in contact lens solutions. In addition, sorbic acid is normally stored at pH=7.0, where it is not stable. At pH=4.0, it is very stable but cannot be instilled into the eye. The present invention will therefore allow solution to be stored at low pH and the pH raised to an ocularly acceptable level as the solution is administered.

Other preservatives that are not directly charged, such as chlorhexadine, could also be removed by the present invention. For example, a size exclusion mechanism may be utilized for removing certain types of preservative compounds. Overall, the term "scavenging material" as used herein refers to all material which will remove or change the nature of preservatives or other components in a solution exiting the container.

From the foregoing description of the invention, it should be seen that the present invention provides the ability to dispense preservative-free solutions from containers housing solutions that are preserved. Whereas the present invention has been described with respect to specific embodiments thereof, it should be understood that various changes and modifications will be suggested to one skilled in the art and it is intended that the invention encompass such changes and modifications that will fall within the scope of the appended claims.

What is claimed is:

1. A method for selectively removing a preservative agent from an opthalmic solution which comprises bringing an opthalmic solution containing a preservative agent into contact with a scavenging means which selectively removes the preservative agent from the opthalmic solution to obtain a preservative agent-free opthalmic solution.

2. A method according to claim 1 wherein said scavenging means is a material having a negative charge and said preservative agent has a positive charge.

3. A method according to claim 1 wherein said scavenging means is a material having a positive charge and said preservative agent has a negative charge.

4. A method according to claim 1 wherein said scavenging means is fumed silica and said preservative agent is a quaternary ammonium compound.

5. A method according to claim 1 wherein said scavenging means is in the form of a porous mass.

6. A method according to claim 5 wherein said porous mass is porous plastic embedded with sulfonated cross-linked styrene divinyl benzene.

7. A method according to claim 1 wherein the opthalmic solution is a wetting solution.

8. A method according to claim 1 wherein the opthalmic solution is a cleaning solution.

9. A method according to claim 1 wherein the opthalmic solution is a soaking solution.

* * * * *